United States Patent [19]
Howell et al.

[11] Patent Number: 5,541,232
[45] Date of Patent: Jul. 30, 1996

[54] TREATMENT OF MULTIDRUG RESISTANT DISEASES

[75] Inventors: Stephen Howell, Del Mar, Calif.; Atul Khandwala, Edgewater, N.J.; Om P. Sachdev, New City, N.Y.; Charles G. Smith, Rancho Santa Fe, Calif.

[73] Assignee: Chemex Pharmaceuticals, Inc., Tarrytown, N.Y.

[21] Appl. No.: 264,740

[22] Filed: Jun. 23, 1994

Related U.S. Application Data

[63] Continuation-in-part of Ser. No. 81,663, Jun. 23, 1993, Pat. No. 5,409,690.

[51] Int. Cl.$^6$ ............................ A61K 31/045; A61K 31/05
[52] U.S. Cl. ................................. 514/731; 514/727
[58] Field of Search ........................ 424/10; 514/731, 514/736

[56] References Cited

U.S. PATENT DOCUMENTS

| | | | |
|---|---|---|---|
| 4,562,298 | 12/1985 | Parkhurst et al. | 568/644 |
| 4,695,590 | 9/1987 | Lippman | 514/724 |
| 4,708,964 | 11/1987 | Allen | 514/433 |
| 4,774,229 | 9/1988 | Jordan | 514/025 |
| 4,880,637 | 11/1989 | Jordan | 424/641 |
| 4,954,659 | 9/1990 | Parkhurst et al. | 568/651 |
| 5,008,294 | 4/1991 | Jordan et al. | 514/731 |

OTHER PUBLICATIONS

Sonneveld, et al., "Modulation of Multidrug–Resistant Multiple Myeloma by Cyclosporin", *The Lancet*, Aug. 1, 1992, vol. 340, No. 8814.

Carter, et al., "Chemotherapy of Cancer", Second Edition, *A Wiley Medical Publication*, 1981, pp. 361–365.

Author: Endicott, et al. Title: The Biochemistry of P–glycoprotein–Mediated Multidrug Resistance Publication: Ann. Rev. Biochem. (1989) 58, 137–171.

Author: Shalinsky, et al. Title: Regulation of Initial Vinblastine Influx by P–glycoprotein Publication: Br. J. Cancer, 67:30–36 (1993).

Author: Gottesman, et al. Title: The Multidrug Transporter, a Double–edged Sword Publication: J. Biol. Chem., 263(25):12163–6 (1966).

Author: Ford, et al. Title: Pharmacology of Drugs that Alter Multidrug Resistance in Cancer Publication: Pharmacol. Rev., 42(3):155–199 (1990).

Author: Murren, et al. Title: Why Haven't We Cured Multidrug Resistance Tumors? Publication: Oncol. Res., 4(1):1–6 (1992).

Author: Choi, et al. Title: An Altered Pattern of Cross–Resistance in Multidrug–Resistant Human Cells results from Spontaneous Mutations in the *mdr1* (P–Glycoprotein) Gene Publication: Cell, 53:549–529 (1989).

Gilman, et al., Goodman and Gilman's The Pharmacological Basis of Therapeutics, Eighth Edition (1990), McGraw Hill, Inc., New York, Section XII, pp. 1202–1263.

Cancer Principles and Practice of Oncology, 4th Ed., J. B. Lippincott Co., 1993, Table 18–1, 326–329.

Poster Presentation given at the national meeting of American Association for Cancer Research, at San Francisco, CA, Apr. 1994. The abstract of this poster has also been published in the Proceedings of American Association for Cancer Research, vol. 35, Abstract No. 2127.

*Primary Examiner*—Theodore J. Criares
*Attorney, Agent, or Firm*—Weiser & Associates

[57] ABSTRACT

A method and composition for treating multidrug resistance in a mammal, in which the composition includes NDGA or an analog of NDGA in accordance with the following formula:

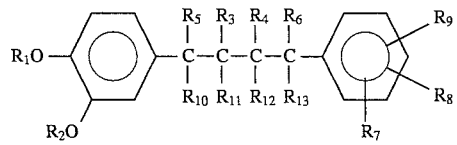

wherein $R_1$ and $R_2$ are independently H, lower alkyl or lower acyl;

$R_3$, $R_4$, $R_5$, and $R_6$ are independently H or lower alkyl;

$R_7$, $R_8$ and $R_9$ are independently H, hydroxy, lower alkoxy or lower acyloxy; and $R_{10}$, $R_{11}$, $R_{12}$ and $R_{13}$ are independently H or lower alkyl, in a pharmaceutically acceptable vehicle.

The method is particularly suitable for administering an antineoplastic agent, and the composition includes the combination of NDGA, or an analog with such an antineoplastic agent.

35 Claims, 5 Drawing Sheets

TREATMENT OF MULTIDRUG RESISTANT DISEASES

RELATED APPLICATION

The patent application is a continuation in part of pending application Ser. No. 08/081,663 filed Jun. 23, 1993 entitled Treatment of Multidrug Resistant Diseases, now U.S. Pat. No. 5,409,690.

FIELD OF INVENTION

This invention relates to a method of preventing development of multidrug resistance (hereinafter MDR) and to a method of reversing MDR if one already exists thereby to prevent or correct drug accumulation defect in drug resistant cells. More particularly, the invention relates to the administration of masoprocol along with antineoplastic/cytotoxic drugs to which cells develop multidrug resistance (MDR), e.g., Doxorubicin, Daunorubicin, Amsacrine Mitoxantrone, Dactinomycin, Ellipticine, Etoposide, Teniposide, Chlorambucil, Melphalan, Cyclophosphamide, Nitrosoureas BCNU, CCNU, MeCCNU), Methotrexate, Trimetrexate, 5-FU, Ara-C, Ara-A, Cisplatin, Carboplatin and Taxol.

REPORTED DEVELOPMENTS

Patients having solid malignant tumors e.g., breast, ovarian, lung, colon and hematological malignant disorders, such as refractory myeloma, often develop MDR. MDR is associated with the overexpression of an MDR-1 gene that codes for a plasma membrane P-glycoprotein. The expression of the MDR-1 gene is believed to be associated with a decreased cellular accumulation of drug due to an active energy dependent efflux mechanism. The active efflux of drug is believed to be mediated by the P-glycoprotein efflux pump.

The problem of multidrug resistance has received quite a lot of attention by research groups as is evidenced by the reports in the scientific literature.

A detailed discussion of multidrug resistance can be found in Endicott, et al., "The Biochemistry of P-glycoprotein—Mediated Multidrug Resistance" *Ann. Rev. Biochem.* (1989) 58, 137–171, incorporated herein by reference. As discussed in the Endicott article, multidrug resistance (MDR) is a unique phenomenon in the study of cellular drug resistance. Cell lines exhibiting this phenotype have been selected for resistance to a single cytotoxic agent, yet they display a broad, unpredictable cross-resistance to a wide variety of unrelated cytotoxic drugs, many of which are used in cancer treatment. The drugs most often involved in MDR are alkaloids or antibiotics of plant or fungal origin, and they include the vinca alkaloids, anthracyclines, epipodophyllotoxins, and dactinomycin. Cross-resistance to alkylating agents such as melphalan, nitrogen mustard, and mitomycin C is occasionally observed. Collateral sensitivity (increased sensitivity) to membrane-active agents such as nonionic detergents, local anesthetics, steroid hormones, and calcium channel blockers often accompanies the development of MDR. The recognition that the emergence of a complex drug resistance phenotype of broad specificity in human tumors could limit successful chemotherapy has provided the impetus to study MDR cell lines as a model for clinical drug resistance.

Kinetic experiments reveal that MDR cells are able to maintain a lowered intracellular drug concentration to a large degree via the increased activity of an energy-dependent drug efflux mechanism. However, many factors may determine the extent of cellular drug accumulation. This is not surprising, given the structural diversity of the compounds involved, their very different pharmacological properties, and the range of their intracellular targets. Drug transport studies indicate that MDR might be mediated by an alteration in the plasma membrane rather than a host of drug-specific enzymatic changes. Early genetic experiments suggested that a single genetic alteration mediates the decreased drug accumulation in MDR cell lines. For example, MDR mutants can be derived by single-step selections with or without mutagenesis, and by DNA-mediated gene transfer. Revertants that have lost the complete MDR phenotype can also be selected in a single step. The product of the mdr1 gene which mediates MDR has been isolated and alternatively called P-glycoprotein, P-170, or the MDR-associated glycoprotein (MDRG). Transfection experiments using either the human or mouse P-glycoprotein cDNA sequence show that increased P-glycoprotein expression is able to confer a complete MDR phenotype on drug-sensitive cells.

It has been reported that cells that overexpress the mdr1 gene have decreased steady state accumulation and increased efflux of many anticancer drugs including VBL, Shalinsky, et al., Regulation of initial vinblastine influx by P-glycoprotein, *Br. J. Cancer,* 67: 30–36 (1993). Shalinsky, et al. also reports that other investigators have also demonstrated the ability of PGP to efflux VBL and doxorubicin in MDR cells.

In the context of this invention, the term "MDR" includes resistance to one or to multiple drugs. The term refers and includes drug "sensitive" cells and drug "resistant" cells.

The analysis of P-glycoprotein cDNA and genomic sequences has led to the proposal of a model for the structure of P-glycoprotein and its involvement in drug transport. The molecule has a tandemly duplicated structure, each half encoding six potential transmembrane domains and the consensus sequences for a nucleotide-binding site. Drugs are proposed to bind directly to P-glycoprotein and then to be actively effluxed from the cell via a pore or channel formed by the molecule's multiple transmembrane domains using energy derived from P-glycoprotein-mediated ATP hydrolysis.

A number of compounds, originally described as calcium channel blockers, calmodulin inhibitors, or lysosomotropic agents, have been found to "reverse" MDR. Many of these drugs are used to treat noncancer patients, and represent a basis upon which to design agents suitable as "chemosensitizers" for the treatment of clinical drug resistance. Expression of P-glycoprotein in human tissues and cancer is also being extensively explored.

Attempts have been made to reverse MDR and to correct the drug accumulation defect in drug resistant cells. Among the agents which show promise in vitro are verapamil, quinidine, amioderone, cyclosporin and certain phenothiazines. It appears, however, that in vivo concentrations necessary to reverse MDR cannot be achieved without substantial toxicity to patients.

Gottlesman, et al., "The Multidrug Transporter, a Double-edged Sword," *J. Biol. Chem.,* 263 (25):12163–6 (1966), discusses multidrug resistance (MDR) in tumor cells in regard to the uptake, metabolism and extrusion of chemotherapeutic agents. The article discusses the action of MDR genes in transporting such agents out of human cancer cells, and the effect of modulators, such as verapamil, on such transport. The article points out the need for further studies.

Ford, et al., "Pharmacology of drugs that Alter multidrug Resistance in Cancer, " *Pharmacol. Rev.*, 42(3):155–199 (1990) in a very detailed publication note that although a tremendous amount has been learned about MDR, considerable work remains to be done to translate these advances into clinical therapeutic gains.

Murren, et al., "Why Haven't We Cured Multidrug Resistant Tumors?" *Oncol. Res.*, 4(1):1–6, (1992) in an article the title of which is revealing, points out that attempts to reverse clinical drug resistance by blockade of P-glycoprotein have not yet been successful.

Choi, et al., "An Altered Pattern of Cross-Resistance in Multidrug-Resistant Human Cells Results from Spontaneous Mutations in the mdr1 (P-Glycoprotein) Gene, " *Cell*, 53:519–529 (1989), discusses mutations of the mdr1 gene in multidrug-resistant cells. The article underscores the complexity of the problem in suggesting that multidrug resistance phenotype may involve yet other genetic changes in addition to an increase in mdr1 expression.

These publications emphasize the seriousness of the problem of MDR and the need for a solution. The present invention contributes to solving the MDR problem.

The treatment of neoplastic disease, i.e., cancers, by the administration of chemotherapeutic agents is discussed in detail in Gilman, et al., *Goodman and Gilman's The Pharmacological Basis of Therapeutics*, Eighth Edition (1990), McGraw-Hill, Inc., New York, Section XII, pages 1202–1263, incorporated herein by reference. Such chemotherapeutic agents, also referred to as antineoplastic agents or drugs may also act as cytotoxic agents for use in the treatment of conditions other than cancer.

Many such antineoplastic agents are listed in the Table XII-1 on pages 1205–7 of Gilman. Another listing of antineoplastic agents may be found in *Cancer Principles and Practice of Oncoloqy*, 4th Ed., J. B. Lippincott Co., 1993, Table 18-1, 326–329, incorporated herein by reference.

Among the antineoplastic agents to which the present invention is directed are those generally classified as plant derivatives including taxol, the epipodophyllotoxins such as etoposide, teniposide and the vinca alkaloids such as vincristine, vinblastine, and vindesine. Another group are the antibiotics, such as dactinomycin, doxorubicin, daunorubicin, idarubicin, mithramycin, mitomycin C, plicamycin and bleomycin. Another general group denominated as antimetabolites include methotrexate, 5-fluorouracil, 5-fluorodeoxyuridine, 6-mercaptopurine, 6-thioguanine, cytarabine (Ara-C), 5-azacytidine, hydroxyurea, deoxycoformycin and fludarabine. Another group, the biological response modifiers includes interferon alpha. Another group is identified as alkylative agents and includes cyclophosphoramide, ifosfamide, melphalan, busulfan, the nitrosoureas, BCNU, CCNU, methyl-CCNU and streptozotocin, chlorambucil, platinum coordination complexes such as cisplatin (cis-DDP) and carboplatin (CBDCA), aziridinylbenzoquinone (AZQ), and triazenes such as dacarbazine (DTIC). Other antineoplastic agents include mAMSA, procarbazine, hexamethylmelamine and mitoxantrone.

The invention is thus directed to these antineoplastic agents and others that are not listed herein or discussed in publications and others that may not yet have been identified to be effective as neoplastic agents.

SUMMARY OF THE INVENTION

In accordance with the method of the present invention, an antineoplastic or cytotoxic agent is administered in combination (before, together and/or after) with NDGA (masoprocol) or an analog of NDGA in accordance with general Formula (I) set forth below, or a pharmaceutically acceptable salt thereof, hereinafter collectively referred to as NDGA compounds.

The NDGA compound and antineoplastic agent can be co-administered simultaneously or sequentially with the NDGA compound preceding and/or following administration of the antineoplastic agent.

The invention also relates to a pharmaceutical or biologically active composition that comprises one or more antineoplastic or cytotoxic agents with NDGA or an analog of NDGA as set forth in said Formula, or a pharmaceutically acceptable salt thereof.

Masoprocol is a new MDR modulating agent. We have discovered that the combination of masoprocol known as nordihydroguaiaretic acid (hereinafter sometimes referred to as NDGA) or certain analogues thereof in combination with cytotoxic agents, e.g., Doxorubicin, Daunorubicin, Amsacrine, Mitoxantrone, Dactinomycin, Ellipticine, Etoposide, Teniposide, Chlorambucil, Melphalan, Cyclophosphamide, Nitrosoureas (BCNU, CCNU, MeCCNU), Methotrexate, Trimetrexate, 5-FU, Ara-C, Ara-A, Cisplatin, Carboplatin and Taxol can overcome multidrug resistance of certain diseased cells and has the potential of being effective in the treatment of solid malignant tumors, e.g., brain, breast, colon, lung, ovarian cancers and hematological malignant disorders including lymphoma, leukemia (acute nonlymphocytic leukemia, acute myelocytic leukemia), or increase the therapeutic effectiveness of the above-mentioned cytotoxic agents.

The naturally occurring meso form of the nordihydroguaiareticetic acid [meso-1,4-bis (3,4-dihydroxyphenyl)-2, 3-dimethylbutane]("NDGA") was reported as providing a positive result against malignant melanoma. C. R. Smart, et al., *Rocky Mountain Medical Journal*, November 1970, pp.39–43. (Unless otherwise indicated, NDGA is used herein to refer to the meso form of nordihydroguaiaretic acid). NDGA is found in the creosote bush, and this plant was used for centuries to brew tea which was the basis for a folk remedy that called for drinking the tea to cure colds, rheumatism and other ailments. However, this remedy has not proven to be successful.

A clinical study was conducted by Smart, et al., reported in U.S. Pat. No. 4,880,637, in which human cancer patients ingested either a tea made from the creosote bush or doses of pure NDGA. This study indicated that neither NDGA nor the tea were effective anticancer agents and in some cases caused stimulation of tumor cell growth. This confirmed the earlier screening studies of NDGA conducted by Leiter, et al. of the Cancer Chemotherapy National Service Center of National Cancer Institute which obtained negative results when NDGA was tested against several types of cancer cells.

It has been reported in U.S. Pat. No. 4,880,637 that NDGA and its analogues in combination with ionic zinc is effective in the treatment of benign, paramalignant and malignant growth of the skin without detrimental side effects associated with chemotherapy or chemosurgical techniques.

NDGA was also reported in U.S. Pat. No. 4,695,590,as having efficacy in retarding senescence or aging in mammals.

To our knowledge, the use of NDGA in combination with other cytotoxic/antineoplastic chemotherapeutic drugs is not known, nor has it been reported to inhibit multidrug resistance associated with the treatment of solid malignant tumors or hematological disorders in mammals.

In the modern clinical oncology practice, it has been established that overexpression of P-glycoprotein (Pgp) in cancer patients is directly related to the increase in the multidrug resistance (MDR) to treatment with presently available chemotherapies. The present inventors have discovered that masoprocol (NDGA) overcomes the Pgp mediated resistance and Pgp antagonism of the cells, thereby increasing the levels of chemotherapeutic drugs which accumulate in the cancer cells.

The present invention provides a method and composition for the inhibition and/or reversal of multidrug resistant phenomenon in a patient and thereby treatment of solid malignant tumors and hematological malignancies comprising the administration of NDGA to said patient preferably in a pharmaceutically acceptable vehicle.

The general formula comprises of from about 0.1% to about 25% NDGA or an analogue thereof in a pharmaceutically acceptable vehicle for topical application or of from about 1 mg NDGA to about 500 mg of NDGA per kg of body weight for systemic administration.

NDGA and its analogues used in the present invention have the following Formula (I):

wherein $R_1$ and $R_2$ are independently H, lower alkyl or lower acyl;

$R_3$, $R_4$, $R_5$ and $R_6$ are independently H or lower alkyl;

$R_7$, $R_8$ and $R_9$ are independently H, hydroxy, lower alkoxy or lower acyloxy; and $R_{10}$, $R_{11}$, $R_{12}$ and $R_{13}$ are independently H or lower alkyl.

Lower alkyl is intended to generally mean $C_1$–$C_6$, alkyl, and preferably $R_3$ and $R_4$ are $C_1$–$C_3$ alkyl. Lower acyl is intended to generally mean $C_1$–$C_6$ acyl, with $C_2$–$C_6$ acyl being preferred. The formula is directed to both the phenolic compounds and the conventional esters and ethers thereof.

DETAILED DESCRIPTION OF THE INVENTION

NDGA and its analogues (also referred to herein as catecholic butanes) according to the present invention, may be made by the synthetic methods provided in U.S. Pat. Nos. 4,562,298 and 4,954,659 which are incorporated herein by reference in their entirety.

Examples of catecholic butanes include: the d-, l-racemic mixture of d- and l-, meso-isomers of 1,4-bis (3,4-dihydroxyphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3',4',5'-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; 1-(3,4-dihydroxyphenyl)-4-phenylbutane and 1-(3,4-dihydroxyphenyl-4-(2,5-dihydroxyphenyl)butane. Mixtures of Formula (I) may be used in the instant composition as well.

Catecholic butanes are described to be useful in the treatment of benign, premalignant, and malignant solid tumors, especially those of the skin. See U.S. Pat. Nos. 4,880,637; 4,697,590; 5,008,294 and 4,708,964. These patents are incorporated herein by reference.

The compositions of the present invention are believed to be effective in the treatment of solid mammalian tumors or hematologic malignancies which can develop multidrug resistance. These solid tumors include cancers of the head and neck, lung, mesothelioma, mediastinum, esophagus, stomach, pancreas, hepatobiliary system, small intestine, colon, rectum, anus, kidney, ureter, bladder, prostate, urethra, penis, testis, gynecological organs, ovarian, breast, endocrine system, skin, central nervous system; sarcomas of the soft tissue and bone; and melanomas of cutaneous and intraocular origin. Hematological malignancies include childhood leukemias and lymphomas, Hodgkin's disease, lymphomas of lymphocytic and cutaneous origin, acute and chronic leukemia, plasma cell neoplasm and cancers in AIDS. The preferred mammalian species to be subjected to the present invention are humans and domesticated animals.

Other neoplastic diseases for which the invention is applicable include those identified in Goodman and Gilman, cited above, and in Anticancer Drugs, also cited above.

The composition and method of the invention are also useful in the treatment of neoplastic diseases that may fail to respond to chemotherapeutic agents de novo or that may become resistant to treatment after an initial response. Likewise, the invention is applicable to cells that have developed or are susceptible to develop drug resistance or multidrug resistance.

The instant compositions can be applied topically, orally or parenterally to the treatment site. When used for topical application, NDGA is usually formulated with a pharmaceutically acceptable carrier. Carrier materials are well known in the pharmaceutical formulation art and include those materials referred to as diluents or vehicles. The carrier may include inorganic or organic materials and should have sufficient viscosity to allow spreading of the composition and provide good adherence to the tissue to which it is topically applied. Examples of such carriers include, without limitation, polyols such as glycerol, propylene glycol, polyethylene glycol, preferably of a molecular weight between about 400 to about 8000, suitable mixtures thereof, vegetable oils, and other materials well known to those skilled in this art. The viscosity of the formulation can be adjusted by methods well known in the art, for example, by the use of a higher molecular weight polyethylene glycol.

In addition to NDGA, the formulation can contain pharmacologically-acceptable additives or adjuvants such as antimicrobial agents, e.g., methyl, ethyl, propyl and butyl esters or parahydroxybenzoic acid as well as chlorobutanol, phenol, ascorbic acid, etc. The formulation can also contain thickening or gelling agents, emulsifiers, wetting agents, coloring agents, buffers, stabilizers and preservatives including antioxidants such as butylhydroxyanisole in accordance with the practice of the art. The formulation can also contain penetration enhancers such as dimethylsulfoxide, long-chain alcohols such as nonoxynol, long-chain carboxylic acids, propylene glycol, N-(2-hydroxyethyl)pyrrolidone, 1-dodecyl-azacycloheptan-2-one, and the like. Depending on the method of application and the disease being treated, it may be desirable to use absorption-delaying agents such as aluminum monostearate and gelatin.

The composition of the formulation can be adjusted using components well-known in the formulation art to provide a pharmaceutical formulation which is a gel, cream, ointment, solid, liquid, semi-solid, etc. The particular physical form of the formulation depends on the desired method of treatment and the patient to be treated.

For administration by injection, the compositions according to the invention are formulated as solutions or suspensions having a low enough viscosity to be injected. The composition suitable for injectable use must be sterile and fluid to the extent that easy syringe injection exists. It should also be stable under conditions of manufacturer and storage and be preserved against contamination by microorganisms. Preservatives include alcohol, benzoic acid, sorbic acid, and methyl and propyl parabin with and without propylene glycol. Additionally, the pH of the composition must be within a range which does not result in tissue damage, namely, between about 3.0–7.5.

The concentration of NDGA in a particular formulation depends on the condition being treated, the method of application, i.e., topical or injection, the rate of delivery of the active ingredient(s) to the treatment site, and the number of applications of the formulation which can be used. Additionally, certain NDGA analogues are more effective in treating particular conditions than are other analogues. The composition of the invention may also include compounds that have been shown to reverse MDR like verapamil or others. The concentration of these compounds, like verapamil in the formulation likewise depends upon the condition being treated and the particular NDGA analogue or combination of analogues being used.

The pH of the formulation is important in assuring stability of NDGA or its analogue as well as assuring that the formulation is physiologically acceptable to the patient. Many of the analogues, and particularly nordihydroguaiaretic acid, are susceptible to oxidation, for example, by air. Such oxidation can result in discoloration of the formulation rendering it unacceptable for pharmaceutical use. These catechols are more stable against oxidation at lower pH levels. Therefore, it is preferred that if the formulation is to be exposed to oxidizing conditions the pH to be maintained below about 7 and preferably below about 6 in order to provide maximum stability for the compound against oxidation. However, if the oxidizing conditions can be avoided, for example, by storage of the formulation under an inert atmosphere such as nitrogen, a higher pH can be used. The pH of the formulation may be maintained through the use of toxicologically-acceptable buffers. Such buffers are well-known in the pharmaceutical formulation art, and include hydrochloric acid buffer, acid phthalate buffer, phosphate buffer and citric acid/sodium citrate buffer.

As described herein, the composition of the invention comprises one or more catecholic butane and an antineoplastic agent. It is to be understood that the catecholic butane and the antineoplastic agent may be administered separately or together, preferably so that the physiological effect of one is concurrent with or overlaps the physiological effect of the other. It is conceivable though that the physiological effects need not overlap. For instance, a catecholic butane may be administrated to the patient followed by an antineoplastic compound, preferably before the physiological effect of the first administered compound has completely worn off; or alternatively, the sequence of administration can be reversed. It is also conceivable that after the administration of a first catecholic butane, followed by an antineoplastic compound, another catecholic compound may be administered alone or together with an antineoplastic compound. One skilled in the art can conceive other variations that will still be within the scope of the invention.

Further, the catecholic butane and antineoplastic agent may be in different pharmaceutical carriers, administered in different manners, and may be sold or otherwise distributed separately from each other. In these illustrations, the combinations of catecholic butane and antineoplastic agent is considered, in accordance with the invention, to be a "unitary" composition.

The amount of catecholic butane which should be administered will depend, among other factors, on the purpose for which it is being used. When the catecholic compound is being administered to prevent or treat multidrug resistance, then an amount sufficient to achieve such prevention or treatment should be administered. In a composition comprising a catecholic butane and an antineoplastic agent, then a sufficient amount of the catecholic butane would preferably be included that will improve the effectiveness or the therapeutic index of the antineoplastic agent. Other amounts can readily be determined by one skilled in the art.

The following non-limiting example will further illustrate the formulations of and use of the present invention.

EXAMPLE 1

Topical Formulation

| Active Ingredient | |
|---|---|
| NDGA | 10 |
| Excipients, Purified water UPS | 48.25 |
| Propylene glycol USP | 12.0 |
| Polyethylene glycol 400 NF | 7.5 |
| Stearyl alcohol NF | 5.0 |
| Light mineral oil NF | 5.0 |
| Synthetic beeswax | 3.5 |
| Isostearyl alcohol | 3.0 |
| Steareth-2 | 2.75 |
| Steareth-21 | 2.25 |
| Xanthum gum NF | 0.40 |
| Methylparaben, NF | 0.16 |
| Sodium bisulfite | 0.10 |
| Propylparaben NF | 0.08 |
| Citric acid USP | 0.01 |

EXAMPLE 2

For systemic administration, NDGA or analogues can be given as a suspension in methocel, buffered saline, i.v. as a sterile injectable and orally as a tablet or a capsule.

The following tests were preformed to determine the effect of NDGA on efflux of doxorubicin (hereinafter sometimes referred to as DOX) for doxorubicin sensitive MCF7/0 and doxorubicin resistant MCF7/ADR human breast adenocarcinoma cells in vitro.

The cells were exposed to 50 μg/ml NDGA for 24 hrs prior to loading with DOX (doxorubicin) at 37° C. Each cell line was loaded with DOX (5 μg×30 min) and selected samples were treated with verapamil (30 μl of a 1 mM solution) at the end of the loading period and then pelleted and suspended in 37° C. PBS. Flow analysis of cell efflux of DOX was collected over 30 minutes using the time parameter. The results are shown in Table I.

TABLE I

NDGA EFFLUX STUDY FOR MCF7/0 AND MCF7/ADR CELL LINES

|  | TREATMENT | MEAN CHANNEL FLUORESCENSE E | % DOX INCREASE w/VERAPAMIL | % DOX INCREASE w/NDGA |
|---|---|---|---|---|
| MCF7/0 No NDGA | DOX | 318.7 | — | — |
|  | DOX + Verapamil | 312.8 | −1.9 | — |
| RX NDGA | DOX | 460.4 | — | 44.5 |
|  | DOX + Verapamil | 435.6 | −5.4 | — |
| MCF7/ADR | DOX | 227.4 | — | — |
|  | DOX + Verapamil | 309.9 | 36.3 | — |
| RX NDGA | DOX | 285.6 | — | 25.6 |
|  | DOX + Verapamil | 365.4 | 27.9 | — |

DOX = Doxorubicin

In the table, the loading of DOX in cells (Mean Channel Fluorescence) and the % value represent the increase of DOX measured in the cells after treatment with verapamil or NDGA.

Two interesting results are seen with this experiment: 1) the MCF7 cells (sensitive) are loading more DOX after NDGA treatment than controls or verapamil treated cells. This is of interest because verapamil has no effect on sensitive cells. 2) In the resistant MCF7/ADR cells there is an augmentation of DOX retention in both NDGA and NDGA + verapamil. The results indicate NDGA will inhibit the efflux of DOX via the p170 (P-glycoprotein) resistance factor. 3) Treatment of multidrug resistant MCF7/ADR and its parent cell line MCF7/0, human breast adenocarcinoma cells line with 50 μg/ml in clonogenic assay resulted in an increased doxorubicin accumulation of 25.6% and 44.5% respectively. In comparison an experiment of the same cell lines with verapamil treatment resulted in a 36% increased accumulation in the doxorubicin resistant cells (i.e., MCF7/ADR) and no increased accumulation of doxorubicin concentration in the parent MCF7/0 cells.

We conclude that NDGA is a novel agent capable of reversing MDR and potentiation of chemotherapeutic activity of doxorubicin in vitro, which can be used to reverse the multidrug resistance in solid malignant tumors and hematological malignancies.

Procedure for P-Glycoprotein (PGP) Function Assay of Doxorubicin Efflux is shown hereunder.

1. Verapamil (GFW=491.1) Make a 1 mM solution by dissolving 4.911 mg of Verapamil per 10 mls of distilled water. Store at room temperature.

2. Doxorubicin (GFW=580) Make a solution of doxorubicin to contain 10 μg/ml. Store frozen at 0° C.

3. Rhodamine 123 (GFW=380.0) Make a 1 mM solution by dissolving 3.808 mg per mls of absolute ethanol. Store at −20° C.

4. NDGA (MW=302.36) Make a solution of NDGA to contain 50 μg/ml. Store frozen at 0° C.

5. MCF7/0 (Doxorubicin sensitive) and MCF7/ADR (Doxorubicin resistant), human breast adenocarcinoma cell lines.

Procedure:

1. Make up 2×10$^6$ cells per ml in PBS. Expose 1 ml of cells to 50 μg of NDGA for 24 hrs at 37° C. prior to loading with Doxorubicin.
2. Add 1 ml of 10 μg/ml doxorubicin, mix and divide into two aliquots.
3. Add 30 μl of verapamil to one aliquot.
4. Incubate both tubes at 37° C. for 30 minutes. P-glycoprotein function is temperature dependent, so do not place tubes on ice afterwards.
5. Centrifuge the tubes at 37° C. for 5 minutes on a fast spin to pellet cells. Resuspend in 1 ml of buffer.
6. Run immediately on the flow cytometer. Excitation 488 nm, emission 560–600 nm. Collect forward and 90° side scatter and PMT4 linear scale. Collect 10,000–50,000 events and calculate the mean channel fluorescence (MCF) for PMT4.
7. Run both samples as close together as possible, and avoid prolonged exposure to room temperature.

Calculations:

1. Express results as percent increase in mean doxorubicin fluorescence in the verapamil-containing sample.

$$\% \, DOX \, increase = \frac{MCF \, DOX/Verapamil - MCF \, DOX \times 100}{MCF \, DOX}$$

Procedural Notes:

1. If rhodamine 123 is used in the place of doxorubicin as fluorescent stain, suspend 2×10$^6$ viable cells in 2 mls of PBS, add 10 μl of rhodamine to the cells, mix, and divide into two equal aliquots. Add verapamil to one tube and incubate as above. Collect green (PMT2) fluorescence.
2. Keep cells at 37° C. Avoid prolonged exposure to room temperature and do not place cells on ice at any step of the procedure.

Table II shows anti-tumor activity of NDGA against various tumor cell lines.

TABLE II

MASOPROCOL - (NDGA) IN VITRO (CYTOTOXICITY) ANTI TUMOR ACTIVITY

| | IC$_{50}$(μm) | | | |
|---|---|---|---|---|
| | One Hour Pulse Treatment | | *Continuous Drug Exposure | |
| Tumor Cell Line | Masoprocol | Doxorubicin | Masoprocol | Doxorubicin |
| Cancer Cells | | | | |
| CAK-1 Renal | 211 | 3.8 | 53.4 | 0.11 |
| DLD-1 Colon | 124 | 3.7 | 0.08 | 0.42 |
| Lung (NCI-H23) | 172 | 9.3 | 0.08 | 0.15 |

TABLE II-continued

MASOPROCOL - (NDGA) IN VITRO (CYTOTOXICITY) ANTI TUMOR ACTIVITY

| | IC$_{50}$(μm) | | | |
|---|---|---|---|---|
| | One Hour Pulse Treatment | | *Continuous Drug Exposure | |
| Tumor Cell Line | Masoprocol | Doxorubicin | Masoprocol | Doxorubicin |
| Lung (LX-1) Chemex | 18 | 26 | | |
| LOX-IMVI Melanoma | 38.4 | 4.8 | 0.08 | 0.09 |
| SNB Glioblastoma | 312 | 0.7 | 0.08 | 0.03 |
| OVCAR3 ovarian | 258 | 13.8 | 35.9 | 0.7 |
| Normal Cells | | | | |
| WI-38 Lung Fibroblasts | 159 | 10.0 | 312 | 0.6 |
| Detroit 551 Skin Fibroblasts | 62.7 | 3.2 | 312 | 5.5 |
| Hs 68 Newborn Foreskin Fibroblasts | 178 | 11.6 | 18 | 0.12 |

*Drug Treatment with observation at 70 hours

EXAMPLE 3

This example demonstrates the modulation of vinblastine (VBL) toxicity and uptake in multidrug resistant tumor cells by the use of NDGA. To investigate whether masoprocol modulates multidrug resistance, a line of multidrug resistant (GRC-1) cells which were derived from parenteral drug sensitive human cervical carcinoma (KB-3-1) cells by transfection of the mdr1 genes were employed. Such transfection was by the method set forth in Choi, et al., Cell 53:519–529, 1989. These cell lines differ only with respect to the overexpression of P-glycoprotein. These tests were designed to examine whether masoprocol modulates tumor cell drug resistance by interfering with P-glycoprotein function. Specifically, the tests examined the uptake at toxicity of vinblastine (VBL), a drug which is known to be a P-glycoprotein substrate. See, Regulation of initial vinblastine influx by P-glycoprotein, Shalinsky, et al., cited above.

Masoprocol was provided by Chemex Pharmaceuticals, Inc. (Fort Lee, N.J.). Tritiated vinblastine ([$^3$H]VBL) (10 Ci mmol$^{-1}$) was purchased from Moravek Biochemicals (Brea, Calif.), stored in the dark at −80° C. and protected from light during the experiments. Dipyridamole (DPM) was provided by Boerhinger Ingelheim Pharmaceuticals, Inc. (Ridgefield, Conn.).

Drug-sensitive KB-3-1 cells and the drug resistant subline (KB-GRC-1) were obtained from Dr. Igor Roninson (University of Illinois, College of Medicine, Chicago, Ill.). Cells were maintained in Dulbecco's modified Eagle's medium supplemented with 10% fetal bovine serum and 2 mM glutamine. The KB-GRC-1 cells were maintained in medium supplemented with 6 ng/ml colchicine.

To demonstrate modulation of VBL uptake, [$^3$H]VBL was added to subconfluent cells growing in 60 mm dishes in 2 ml culture medium or medium containing the concentrations of masoprocol. At the desired time, the medium was aspirated and cells washed 5 times with ice cold PBS. Cells were digested overnight in 1N NaOH, at which time aliquots were used to determine protein content and radioactivity. The final concentration of VBL was 6 nM.

To demonstrate modulation of VBL toxicity, the inhibiting effect on coding formation was studied. First, cells which had been seeded at 200–300 cells/dish were incubated in media containing masoprocol or VBL. After an incubation period of 10 days at 37° C. the cells were fixed with methanol and stained with Giemsa, and the number of colonies per dish were counted and expressed as a percent of the number of colonies in control conditions. The IC$_{50}$ represents the concentration resulting in 50% inhibition of colony formation. Parenthesis indicate standard deviations determined from replicate experiments.

| | IC$_{50}$ (μM Masoprocol) | IC$_{50}$ (nM VBL) |
|---|---|---|
| KB-3-1 | 43.6 (2.9) | 1.38 (0.46) |
| GRC-1 | 66.8 (7.7) | 52.2 (11.6) |

In contrast to large differences in sensitivity to VBL, both the multidrug resistant GRC-1 cells and the non-resistant KB-3-1 cells are similar in sensitivity to masoprocol.

Thus, unlike VBL, masoprocol is not a substrate for P-glycoprotein. This is an important initial finding which is discussed further below.

EXAMPLE 4

Figure 1:
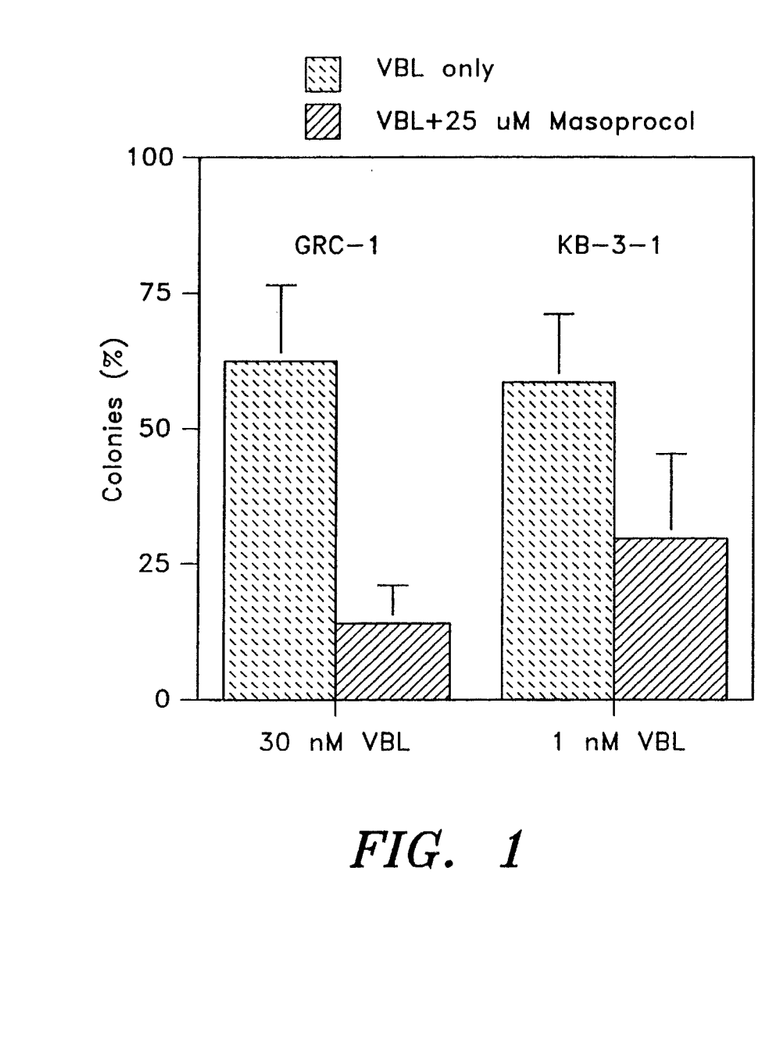
FIG. 1 is a graphical representation showing the effect of masoprocol on vinblastine toxicity in two different cell lines.

To test the modulation of VBL toxicity by masoprocol, cells which had been seeded at 200–300 cells/dish were incubated in media containing various concentrations of VBL in the absence or presence of 25 μM masoprocol. After an incubation period of 10 days at 37° C. the cells were fixed and stained, and the number of colonies per dish were counted and expressed as a percent of the number of colonies formed in control conditions. The results are shown in Figure. 1. Vertical bars are +/− S.D.

For both cell lines, exposure to 25 μM masoprocol increases the effect of VBL on colony formation. Thus, masoprocol treatment results in an increase in the cytotoxicity of VBL in both cell lines.

These results suggest that a typical compound of the invention, like masoprocol, increases the therapeutic index of a typical anticancer drug like VBL. Further, it is noteworthy, that with respect to normal cells as opposed to cancer cells, masoprocol is less toxic than doxorubicin. This is an important finding since the compounds used in the invention could permit use of higher dosages of the anticancer drug, especially with normal cells which are susceptible to or prone to develop MDR.

This also suggests that the compounds used in the invention may be used in a prophylactic and not only therapeutic treatment of the patient. Thus, masoprocol as a typical compound used in the invention is useful for instance in the treatment of malignancies not yet established but diagnosed potentially as cancerous or in areas of the body of the patient which are at risk of the disease. Thus, the method and composition are believed to be useful in the treatment of benign, premalignant and malignant solid tumors, especially those of the skin.

EXAMPLE 5

Several tests were conducted to demonstrate the modulation of VBL uptake. The following test shows the steady state accumulation of VBL.

Cells were incubated for one hour with media containing either tritiated vinblastine ($^3$H]VBL) alone or containing [$^3$H]VBL with 50 μM masoprocol. Cells were then washed with ice cold PBS and the amount of VBL accumulated in cells was determined using a scintillation counter. In FIG. 1 each data point represents the mean of replicate experiments performed with duplicate cultures. Vertical bars are +/− S.D.

The data indicates that relatively low concentrations of masoprocol result in a dose-dependent increase in the steady state accumulation of VBL. Thus, masoprocol increases the steady-state accumulation of VBL. The effect of 50 μM masoprocol is comparable to that of 10 μM verapamil, a known modulator of VBL accumulation.

EXAMPLE 6

Figure 3A:
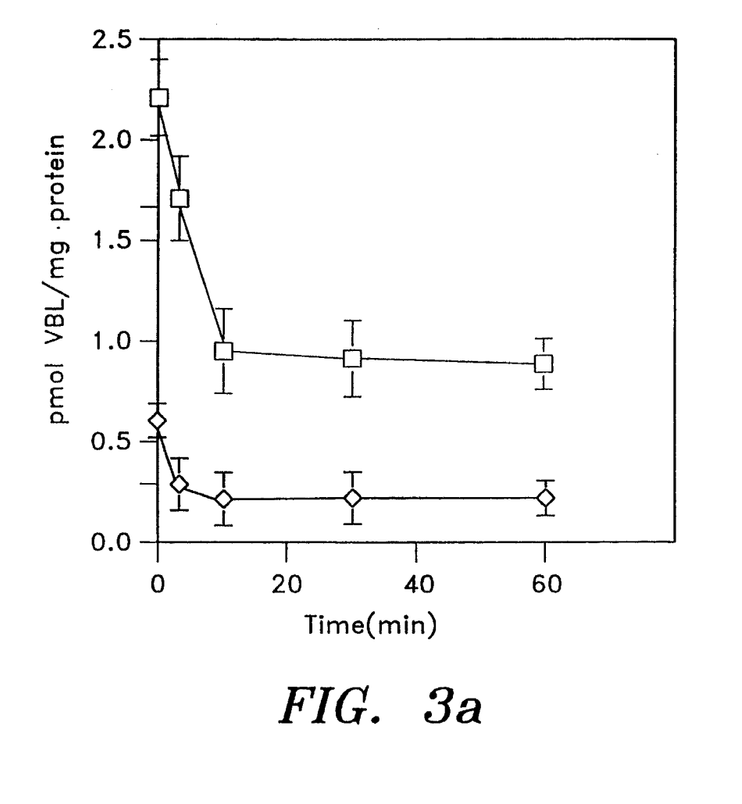
FIGS. 3a and 3b are graphical representations of the effects of masoprocol on vinblastine efflux from GRC-1 cells and KB-3-1 cells, respectively.
Figure 3B:
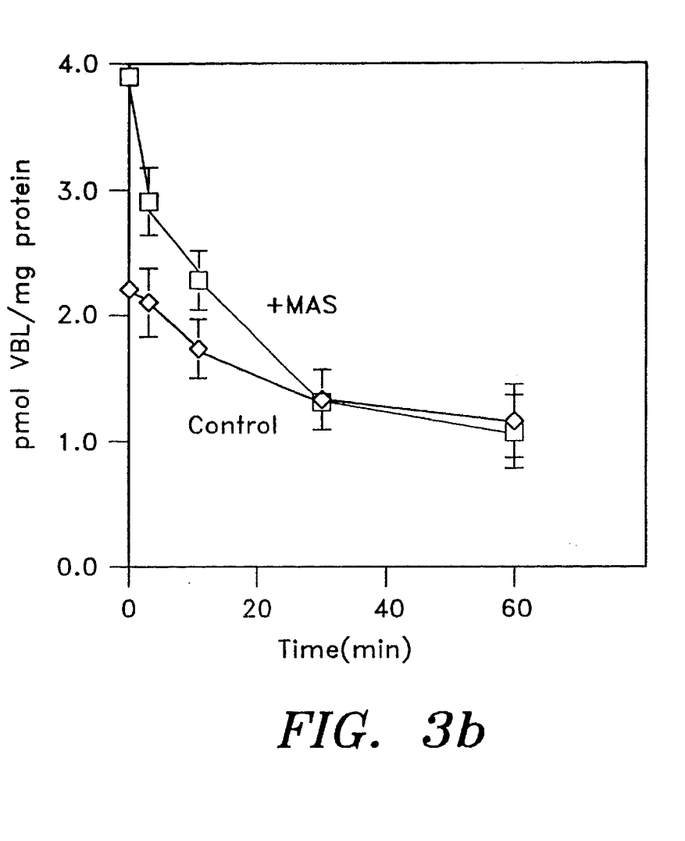
Figure 3C:
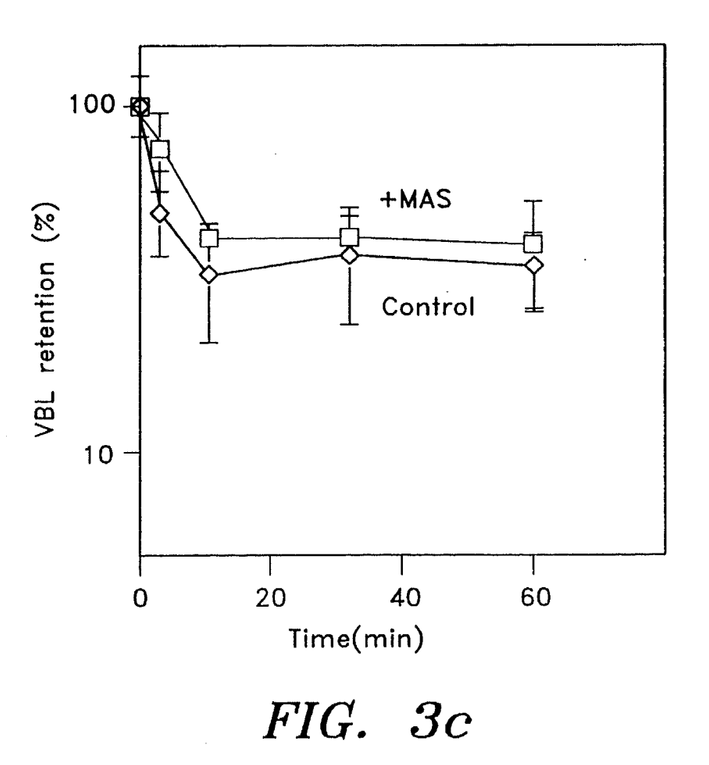
FIGS. 3c and 3d are graphical representations of the effects of masoprocol on vinblastine retention in GRC-1 cells and KB-3-1 cells, respectively.
Figure 3D:
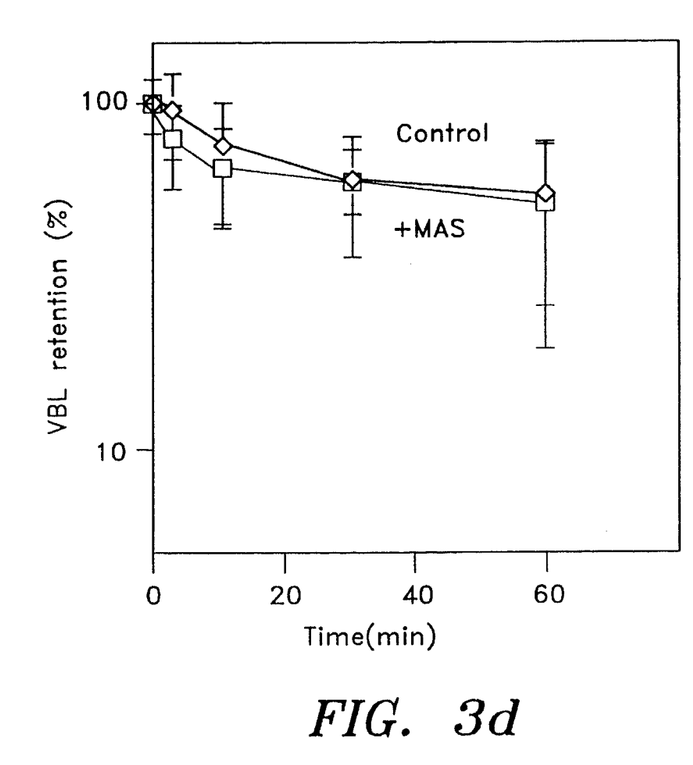

A further test was conducted to show the effect of masoprocol on the efflux of VBL from cells. Cells were incubated with [$^3$H]VBL with or without 50 μM masoprocol for 2 hours. The medium was then replaced with drug-free medium. After incubation for various times, the amount of VBL remaining in the cells was determined as described above. The data was presented in terms of the percentage of VBL remaining at various efflux times compared to VBL in cells with an efflux time of zero. In FIGS. 3a and 3b, efflux is expressed as pmol VBL. In FIGS. 3c and 3d, efflux is expressed as percentage of VBL levels at time zero.

At efflux time zero, the VBL levels are higher in masoprocol-treated cells than in cells not treated with masoprocol (FIG. 3a,b). However, the percent of VBL retained at various efflux time points is not affected by masoprocol treatment (FIG. 3c,d).

Masoprocol thus, does not modulate VBL efflux in these cells. This is another important finding suggesting that without intending to be bound by any particular theory, masoprocol may function differently than known drugs like VBL which are believed to reverse MDR phenotype by virtue of their ability to bind PGP and inhibit efflux activity.

EXAMPLE 7

Figure 4A:
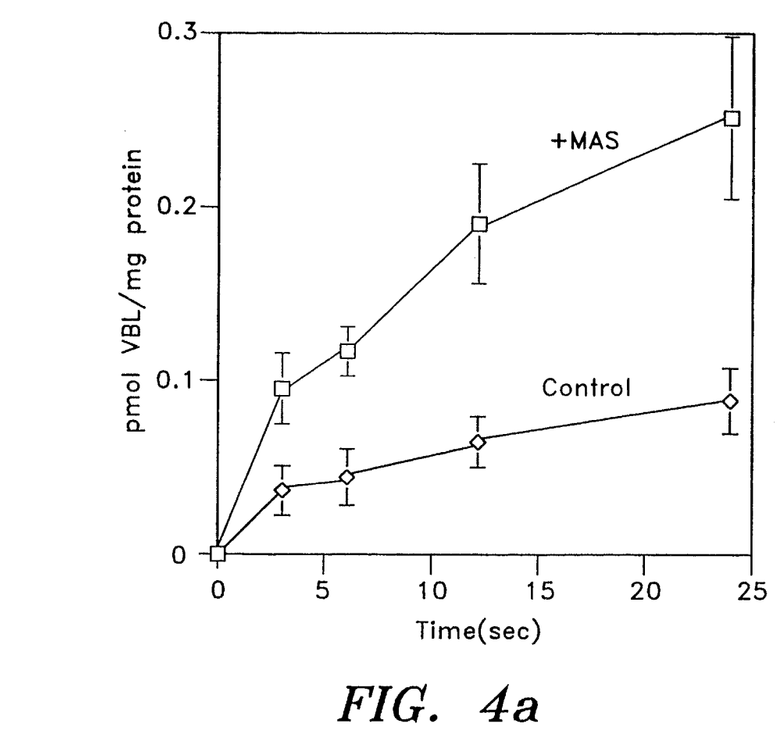
FIGS. 4a and 4b are graphical representations of the effects of masoprocol on vinblastine uptake in GRC-1 cells and KB-3-1 cells, respectively.

A further test was conducted to show the effect of masoprocol on the initial influx of VBL. Cells were exposed to media containing [$^3$H]VBL with and without 50 μM masoprocol. After incubation times ranging from 3 seconds to 24 seconds, the media was removed. The amount of VBL taken up by the cells was determined as described in A. The data was summarized from four replicate experiments. FIG. 4a presents the results for the GRC-1 cell line, and FIG. 4b for the KB-3-1 cell line.

Figure 4B:
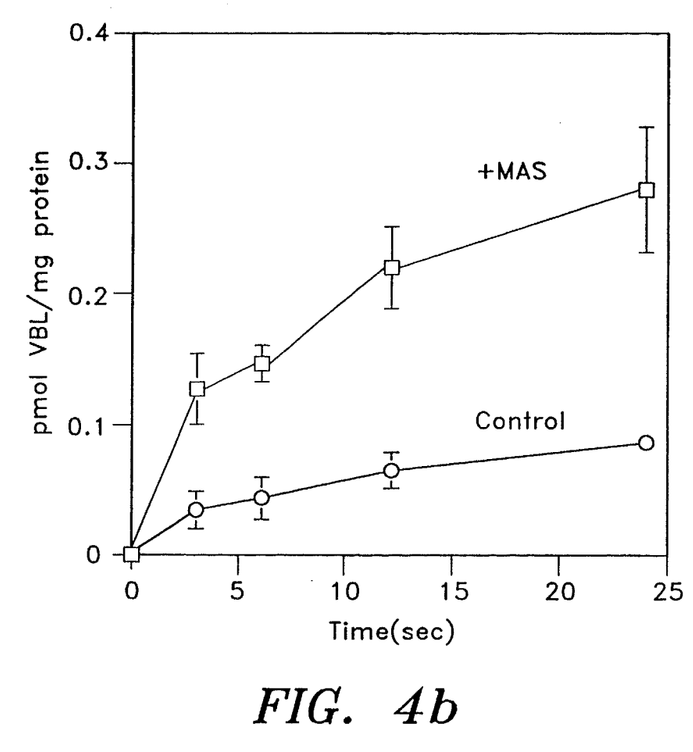

It can be seen that in masoprocol, when added concurrently with VBL, results in a substantial increase in initial VBL uptake. The magnitude of the effect of 50 μM masoprocol is similar to that of 20 μM dipyridamole, a known modulator of VBL influx.

From these results it can be concluded that masoprocol is an effective modulator of initial VBL influx.

These studies suggest that a typical compound of the invention like masoprocol increases the steady state accumulation of VBL in both the multidrug resistant GRC-1 cells and parental KB-3-1 cell lines. Further, masoprocol promotes the initial uptake of VBL. Concurrent exposure to masoprocol increases the cytotoxic effect of VBL in both cell lines. However, masoprocol does not influence the rate of efflux of VBL from these cells, suggesting that it does not influence the function of p-glycoprotein, like VBL.

EXAMPLE 8

MODULATION OF CISPLATIN UPTAKE

Figure 5:
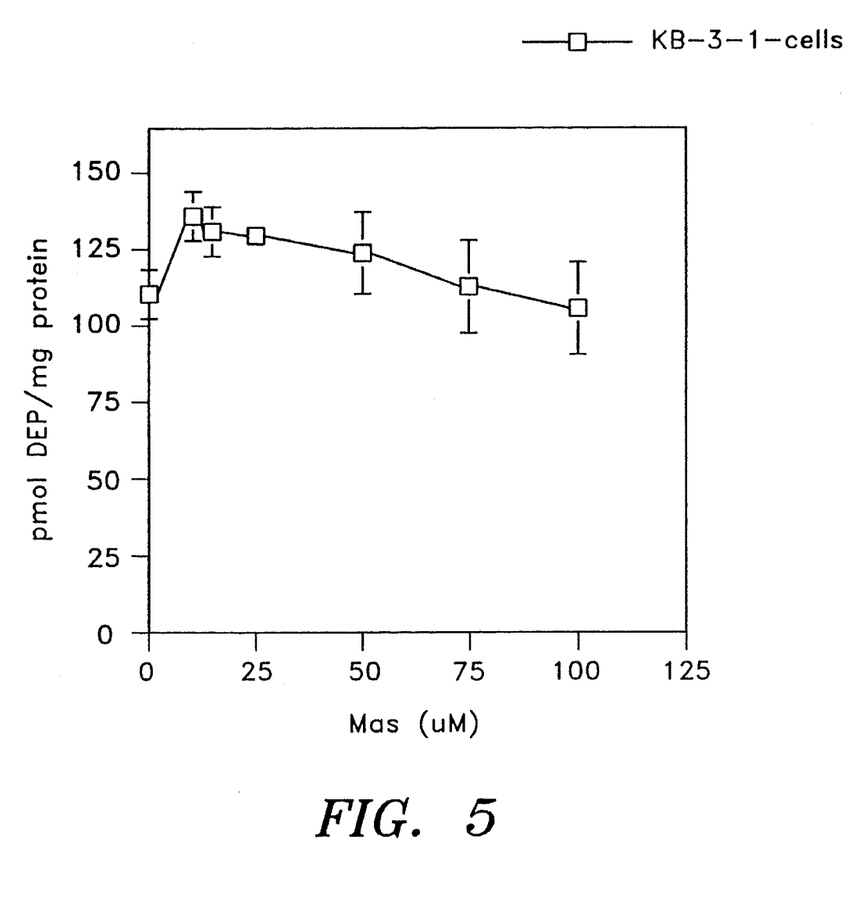
FIG. 5 is a graphical representation of the effect of masoprocol on the uptake of cisplatin in KB-3-1 cells.

Subconfluent cultures of KB-3-1 cells were incubated with [$^3$H]cisplatin (cis-DDP) in culture medium or in medium containing the indicated concentrations of masoprocol as presented in FIG. 5. After one hour incubation, the medium was aspirated and the cells washed 5 times with ice cold PBS. Cells were digested overnight in 1N NaOH, at which time aliquots were used to determine protein content and radioactivity. The final concentration of cisplatin was 5 μM. Each data point represents the mean of triplicate dishes from replicate experiments. The vertical bars are +/− standard deviations.

Figure 2:
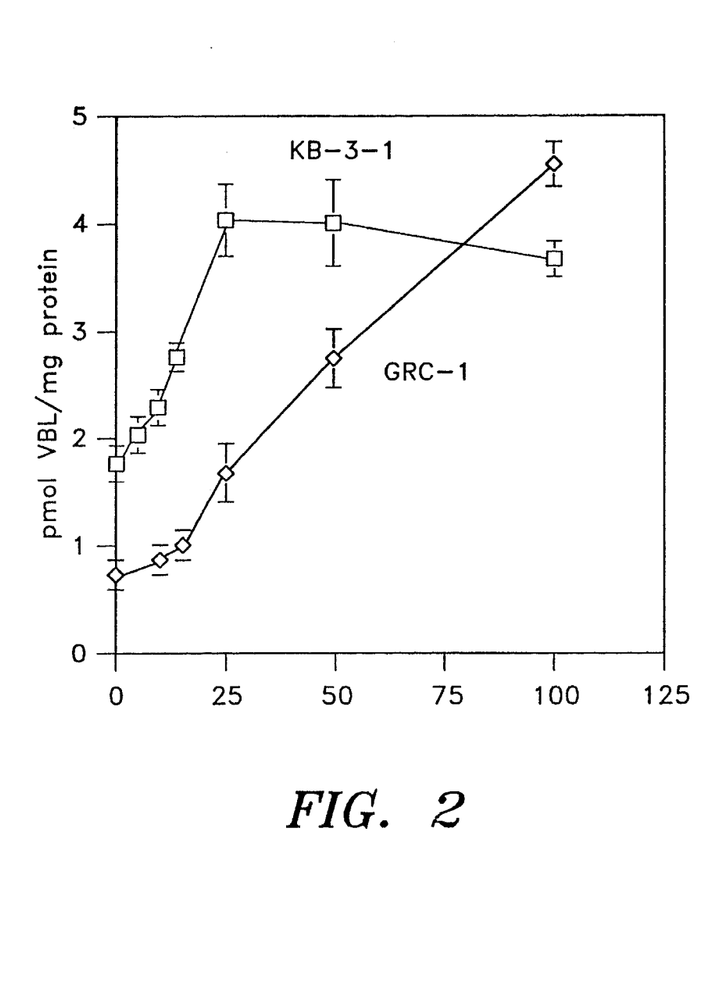
FIG. 2 is a graphical representation showing the effect of masoprocol on steady state accumulation of vinblastine in the same cell lines used in FIG. 1.

The graph in FIG. 5 indicates that the masoprocol treatment increases the uptake of cisplatin by about 25%. The "plateau" of the curve can be seen to mimic the effect of masoprocol on vinblastine (VBL) uptake. See FIG. 2.

It has been reported that an antibiotic cyclosporin can circumvent multiple myeloma clinical resistance to VAC (vincristine, doxorubicin and dexamethasone). Modulation of multidrug-resistant multiple myeloma by cyclosporin, Sonneveld, et al., The Lancet, Vol. 340, No. 8814, Aug. 1, 1992.

In accordance with the invention VBL can be substituted by vincristine in Example 3. It can be conceived that masoprocol can have comparative effects on vincristine as it does on VBL.

In U.S. Pat. No. 4,880,637 and the other patents relating to catecholic butanes, it is shown that a variety of such butanes are effective in the treatment of disorders of the skin, like psoriasis, acne, active keratosis, skin wounds warts, bacterial infections, fungal and viral infections, and solid mammalian tumors illustratively listed in said patents. Several of these catecholic butanes have been found to be particularly effective against human breast adenocarcinoma including NDGA. These butanes, in addition to NDGA, include the following: d,l NDGA; NDGA Tetracetate; NDGA Tetrapropionate; 1,4-bis(3'-methoxy-4'-hydroxyphenyl butane; 1,4-bis(3'-methoxy-4'-hydroxyphenyl)-2,3-dimethyl butane; 1-(3',4'-dihydroxyphenyl)-4-(2',3',4'-trihydroxyphenyl)-butane; 1-(3',4'-dihydroxyphenyl)-4(3',4',5'-trihydroxyphenyl)-butane; 1-(3',4'-dihydroxyphenyl)-4-(2', 5'-dihydroxyphenyl)-butane; and 1-(3',4'-dihydroxyphenyl)-4-phenyl butane.

When these butanes are substituted for NDGA in the tests presented herein, it is expected that comparative effects will be observed on VBL or on a VAD compound. Likewise, other antitumor compounds can be used in accordance with the invention with NDGA or with other catecholic butanes. The selection of a particular antitumor compound will readily be carried out by one skilled in the art since the literature provides adequate guidance regarding which anticancer compound(s) is particularly well suited for the particular cancerous condition which is sought to be alleviated.

As various changes might be made in the formulation and method of the invention herein disclosed, without departing from the spirit and principles of the invention, it is understood that all matter herein described shall be deemed illustrative.

What is claimed is:

1. A pharmaceutical composition for the prevention or treatment of multidrug resistance in cancer cells of a patient, which cells are susceptible to multidrug resistance or which cells have become multidrug resistant, comprising a compound of the formula or a pharmaceutically acceptable salt therof:

wherein $R_1$ and $R_2$ are independently H, lower alkyl or lower acyl;

$R_3$, $R_4$, $R_5$ and $R_6$ are independently H or lower alkyl;

$R_7$, $R_8$ and $R_9$ are independently H, hydroxy, lower alkoxy or lower acyloxy; and $R_{10}$, $R_{11}$, $R_{12}$ and $R_{13}$ are independently H or lower alkyl, and an antineoplastic agent other than the compound, to which antineoplastic agent the cancer cells of the patient are susceptible to multidrug resistance or have developed multidrug resistance, in a pharmaceutically acceptable vehicle.

2. The pharmaceutical composition of claim 1 wherein said lower alkyl is $C_1$–$C_6$ alkyl and said lower acyl is $C_1$–$C_6$ acyl.

3. The pharmaceutical composition of claim 1 wherein said compound is selected from the group consisting of: d-, 1-racemic mixture of d- and 1-, meso-isomers of 1,4-bis(3,4-dihydroxyphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3',4',5'-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; 1-(3,4-dihydroxphenyl)-4-phenylbutane and 1-(3,4-dihydroxyphenyl-4-(2,5-dihydroxyphenyl)butane.

4. The pharmaceutical composition of claim 1 in a solid form.

5. The pharmaceutical composition of claim 1 in a liquid form.

6. The pharmaceutical composition of claim 1 in an injectable form.

7. The pharmaceutical composition of claim 1 for topical administration.

8. A composition for treating multidrug resistance in cancer cells of patient, which cells are susceptible to multidrug resistance or which cells have become multidrug resistant, which comprises a catecholic butane of the formula of claim 1 or a pharmaceutically acceptable salt thereof, an antineoplastic compound to which the cells are susceptible to developing multidrug resistance or to which the cells have developed multidrug resisitance, and a biologically acceptable carrier.

9. The composition of claim 8 wherein the catecholic butane is selected from the group defined in claim 3.

10. The composition of claim 9 wherein the catecholic butane is selected from the group selected from the following: NDGA; d,l NDGA; NDGA tetracetate; NDGA tetrapropionate; 1,4-bis(3'-methoxy-4'-hydroxyphenyl butane; 1,4 -bis(3'-methoxy-4'-hydroxyphenyl)-2,3-dimethyl butane; 1-(3',4'-dihydroxyphenyl)-4-(2',3',4'-trihydroxphenyl)-butane; 1-(3',4'-dihydroxyphenyl)-4(3',4',5'-trihydroxyphenyl)-butane; 1-(3',4'-dihydroxyphenyl)-4-(2',5'-dihydroxyphenyl)-butane; and 1-(3',4'-dihydroxyphenyl)-4-phenyl butane.

11. The composition of claim 10 wherein the catecholic butane is NDGA.

12. The composition of claim 11 wherein the antineoplastic compound is selected from the group consisting of a vinca alkaloid, an antibiotic or a platinum coordination complex.

13. The composition of claim 12 wherein the antineoplastic compound is vinblastine.

14. The composition of claim 12 wherein said antibiotic is doxorubicin.

15. The composition of claim 12 wherein said platinum coordination complex is cisplatin.

16. The composition of claim 12 wherein the catecholic butane is NDGA and the antineoplastic compound is vinblastine, doxorubicin or cisplatin.

17. A method for preventing or inhibiting multidrug resistance in cancer cells of a patient, which cells are susceptible to multidrug resistance or which cells have become multidrug resistant, comprising the administration to said patient of a pharmaceutical composition comprising a compound of the formula or a pharmaceutically acceptable salt thereof:

wherein $R_1$ and $R_2$ are independently H, lower alkyl or lower acyl;

$R_3$, $R_4$, $R_5$ and $R_6$ are independently H or lower alkyl;

$R_7$, $R_8$ and $R_9$ are independently H, hydroxy, lower alkoxy or lower acyloxy; and $R_{10}$, $R_{11}$, $R_{12}$ and $R_{13}$ are independently H or lower alkyl, in a pharmaceutically acceptable vehicle, which composition is administered in combination with an antineoplastic or cytotoxic agent to which the cells are susceptible to developing multidrug resistance or to which the cells have developed multidrug resistance.

18. The method of claim 17 wherein said lower alkyl is $C_1$–$C_6$ alkyl and said lower acyl is $C_1$–$C_6$ acyl.

19. The method of claim 17 wherein said compound is selected from the group consisting of: d-,1-racemic mixture of d- and 1-, meso-isomers of 1,4-bis(3,4 -dihydroxyphenyl)-2,3-dimethylbutane; 1,4-bis(3,4-dihydroxyphenyl)butane; 1,4-bis(3,4-dimethoxyphenyl)-2,3-dimethylbutane; 1,4-bis(3,4-diethoxyphenyl)-2,3-dimethylbutane; 1,4-bis(3,4-dipropoxyphenyl)-2,3-dimethylbutane; 1-(3,4-dihydroxyphenyl)-4-(3',4',5'-trihydroxyphenyl)butane; 1,4-bis(3,4-diacetoxyphenyl)-2,3-dimethylbutane; 1,4-bis(3,4-dipropionyloxyphenyl)-2,3-dimethylbutane; 1,4-bis(3,4-dibutyroyloxyphenyl)-2,3-dimethylbutane; 1,4-bis(3,4-divaleroyloxyphenyl)-2,3-dimethylbutane; 1,4-bis(3,4-dipivaloyloxyphenyl)-2,3-dimethylbutane; 1,4-bis(3,4-dineopentylcarboxylphenyl)-2,3-dimethylbutane; 1-(3,4-dihydroxyphenyl)-4-phenylbutane and 1-(3,4-dihydroxyphenyl-4-(2,5-dihydroxyphenyl)butane.

20. The method of claim 17 wherein said multidrug resistance treatment is in conjunction with the treatment of mammalian tumors and malignancies selected from the group comprising: head and neck cancer, lung cancer, mesothelioma cancer, mediastinum cancer, esophagus cancer, stomach cancer, pancreas cancer, hepatobiliary system cancer, small intestine cancer, colon cancer, rectum cancer, anus cancer, kidney cancer, ureter cancer, bladder cancer, prostate cancer, urethra cancer, penis cancer, testis cancer, cancer of gynecological organs, ovarian cancer, breast cancer, endocrine system cancer, skin cancer, central nervous system cancer, soft tissue sarcoma, bone sarcoma, cutaneous melanomas, intraocular melanoma, childhood leukemias and lymphomas, Hodgkin's disease, lymphomas of lymphocytic lymphoma, cutaneous lymphoma, acute and chronic leukemia, plasma cell neoplasm and cancers in AIDS.

21. The method of claim 17 wherein said composition is in a solid form.

22. The method of claim 17 wherein said composition is in a liquid form.

23. The method of claim 17 wherein said composition is in an injectable form.

24. The method of claim 17 wherein said composition is for topical administration.

25. The method of claim 15 wherein said composition for topical administration is in the form of an emollient.

26. The method of claim 15 wherein said composition for topical administration is in the form of a cream.

27. The method of claim 15 wherein said composition for topical administration is in the form of an ointment.

28. The method of claim 15 wherein said composition for topical administration is in the form of a liposomal preparation.

29. The method of claim 15 wherein said composition for topical administration is in the form of a membrane patch.

30. A method for treating multidrug resistance in solid tumor cells of a patient, which cells are susceptible to multidrug resistance or which cells have become multidrug resistant, which comprises administering to the patient the composition of claim 8.

31. The method of claim 30 wherein the catecholic butane is defined in claim 10.

32. The method of claim 31 wherein the antineoplastic compound is selected from the group consisting of a vinca alkaloid, an antibiotic or a platinum coordination complex and the catecholic butane is NDGA.

33. The method of claim 32 wherein the antineoplastic compound is vinblastine, doxorubicin or cisplatin.

34. The method of claim 33 wherein the administration of the composition increases the apparent initial uptake and accumuation of vinblastine in the cells.

35. The method of claim 34 wherein the administration of the composition does not promote the apparent rate of efflux of vinblastine from the cells.

* * * * *

UNITED STATES PATENT AND TRADEMARK OFFICE
CERTIFICATE OF CORRECTION

PATENT NO. : 5,541,232
DATED : July 30, 1996
INVENTOR(S) : Howell et al.

It is certified that error appears in the above-indentified patent and that said Letters Patent is hereby corrected as shown below:

On the cover page, item 75, line 3, change "SACHDEY" to --SACHDEV--.

Signed and Sealed this

Twelfth Day of November, 1996

Attest:

BRUCE LEHMAN

Attesting Officer     Commissioner of Patents and Trademarks